(12) United States Patent
Lee

(10) Patent No.: US 6,725,728 B1
(45) Date of Patent: Apr. 27, 2004

(54) FINGER GRIPPING FORCE MEASURING OR TESTING DEVICE

(76) Inventor: Mike Chien Ming Lee, P.O. Box 63-298, Taichung (TW)

( * ) Notice: Subject to any disclaimer, the term of this patent is extended or adjusted under 35 U.S.C. 154(b) by 0 days.

(21) Appl. No.: 10/307,382

(22) Filed: Nov. 26, 2002

(51) Int. Cl.[7] .................................................. G01N 3/08
(52) U.S. Cl. ......................................................... 73/824
(58) Field of Search ................................ 73/824, 379.01, 73/379.02, 146.8; 604/30, 141; 264/314; 600/587, 485; 623/25; 482/5; 16/431; 2/20

(56) References Cited

U.S. PATENT DOCUMENTS

| | | | | |
|---|---|---|---|---|
| 3,906,939 A | * | 9/1975 | Aronson ................ 128/2.05 G |
| 4,539,005 A | * | 9/1985 | Greenblatt .................. 604/141 |
| 4,949,729 A | * | 8/1990 | Haski .......................... 128/774 |
| 5,885,509 A | * | 3/1999 | Kristinsson ................. 264/314 |
| 6,086,516 A | * | 7/2000 | Santos ............................. 482/5 |

* cited by examiner

Primary Examiner—Edward Lefkowitz
Assistant Examiner—Octavia Davis

(57) ABSTRACT

A testing device includes a bladder coupled to a pressure gauge, for being squeezed or compressed by users to force air to the pressure gauge, and to measure gripping force of the users. A pumping device may be coupled to the bladder for pumping the bladder to the required pressure. A valve may be coupled between the pumping device and the bladder to control the pumping device. Two pivotal casings may be attached onto the bladder for pressing the bladder, and have flaps to be forced toward each other against the bladder.

12 Claims, 14 Drawing Sheets

FINGER GRIPPING FORCE MEASURING OR TESTING DEVICE

BACKGROUND OF THE INVENTION

1. Field of the Invention

The present invention relates to a testing device, and more particularly to a device for measuring or testing finger gripping forces of users.

2. Description of the Prior Art

Typical exercisers or testing devices may be used for training or testing the muscle groups of the arms of the users. No testing devices have been developed or provided for measuring or testing the finger gripping forces of the users.

The present invention has arisen to mitigate and/or obviate the afore-described disadvantages of the conventional testing devices.

SUMMARY OF THE INVENTION

The primary objective of the present invention is to provide a device for measuring or testing finger gripping forces of users.

In accordance with one aspect of the invention, there is provided a testing device comprising a pressure gauge, and a bladder coupled to the pressure gauge, to force air to the pressure gauge. The bladder is provided to be squeezed by users to measure gripping force of the users.

The bladder includes a port provided therein, the pressure gauge includes a coupler engaged into the port of the bladder for coupling and attaching the pressure gauge to the bladder.

A device may further be provided for pumping the bladder, and includes a pumping device coupled to the bladder to pump the bladder to required pressure, a valve coupled between the pumping device and the bladder, and a knob attached to the valve to control and to open and to close the valve. The pumping device includes a check valve for allowing air to flow into the pumping device and for preventing air from flowing out of the pumping device.

A pressing device may further be provided and attached onto the bladder for pressing the bladder, and includes a pair of casings engaged onto the bladder, and having a first side pivotally secured together, and having a flap extended from the second side, for allowing the flaps to be forced toward each other against the bladder.

The pressure gauge includes a front portion having a graduation provided thereon, a pointer rotatably attached thereto to indicate the graduation, a cover attached to the front portion thereof, and a second pointer rotatably attached to the cover. The cover includes a knob secured to the second pointer for rotating the second pointer relative to the cover and the graduation.

The pressure gauge includes a peripheral fence having a peripheral recess formed therein, the cover includes a peripheral rib rotatably received in the peripheral recess of the peripheral fence for rotatably securing the cover to the peripheral fence of the pressure gauge.

Further objectives and advantages of the present invention will become apparent from a careful reading of a detailed description provided hereinbelow, with appropriate reference to accompanying drawings.

DETAILED DESCRIPTION OF THE PREFERRED EMBODIMENT

Figure 3:
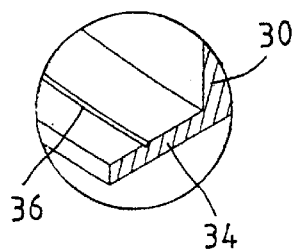
FIGS. 3 and 4 are enlarged partial perspective views of the finger gripping force measuring or testing device, in which some portions of the elements have been cut off.

Referring to the drawings, and initially to FIGS. 1–5, a finger gripping force measuring or testing device in accordance with the present invention comprises a resilient and hollow bladder 10 including one or more, such as two mouths or ports 11, 12 provided therein, and communicating with an inner chamber 13 thereof, for allowing air or fluid to flow into and out of the chamber 13 of the bladder 10.

The bladder 10 is preferably made of resilient rubber or synthetic materials, for allowing the bladder 10 to be compressed or squeezed by users. A pumping device 20, such as a hand pump (FIGS. 1, 2, 5–8) may be selectively or optionally coupled to one of the ports 11 of the bladder 10 with a valve 22 which includes a control knob 21 attached thereto, to control or to open or to close the valve 22.

The pumping device 20 may be used to pump air or fluid into the bladder 10 when required. For example, when the air or fluid pressure within the bladder 10 and the pumping device 20 is small or less, the pumping device 20 may be used to pump air or fluid into the bladder 10 to the required pressure.

The pumping device 20 may include a check valve 23 engaged therein and spaced from the valve 22 for allowing air or fluid to flow into the bladder 10 and the pumping device 20 only, and for preventing air or fluid to flow out of the bladder 10 and the pumping device 20, and thus for allowing the pumping device 20 to pump the bladder 10 and the pumping device 20 to the required pressure.

Figure 4:
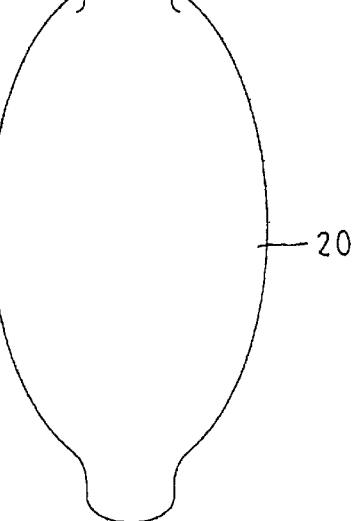
Figure 1:
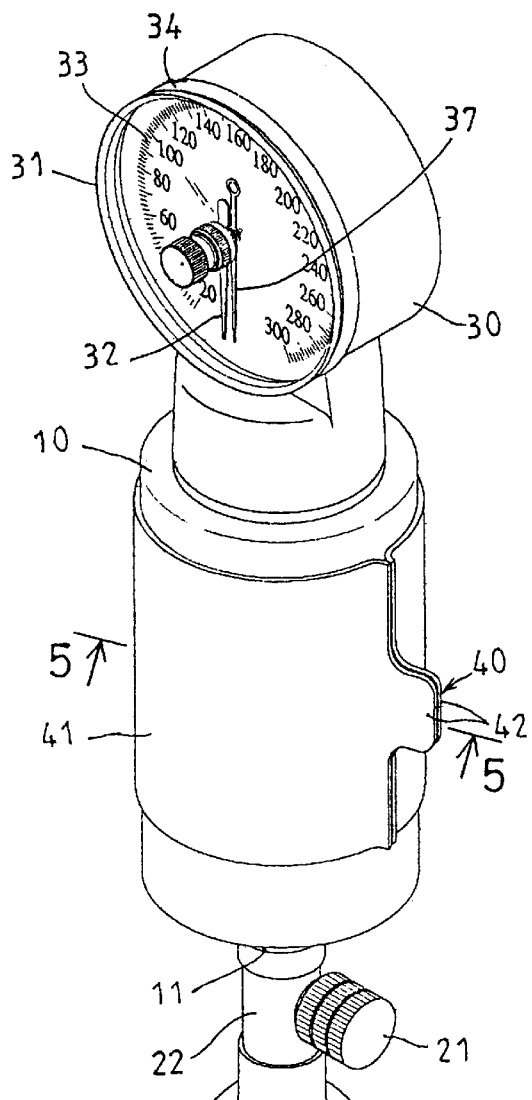
FIG. 1 is a perspective view of a finger gripping force measuring or testing device in accordance with the present invention.
Figure 2:
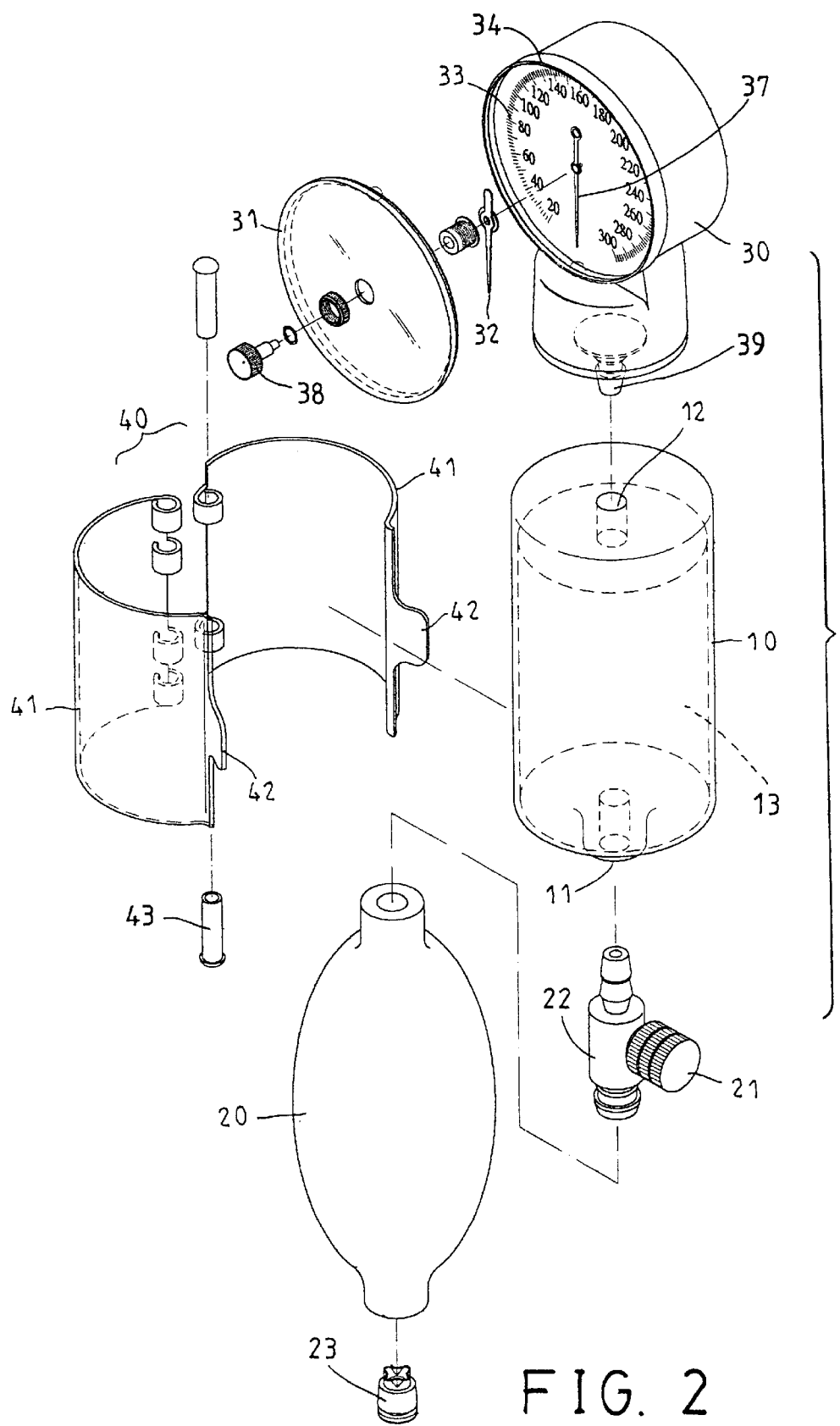
FIG. 2 is an exploded view of the finger gripping force measuring or testing device.
Figure 5:
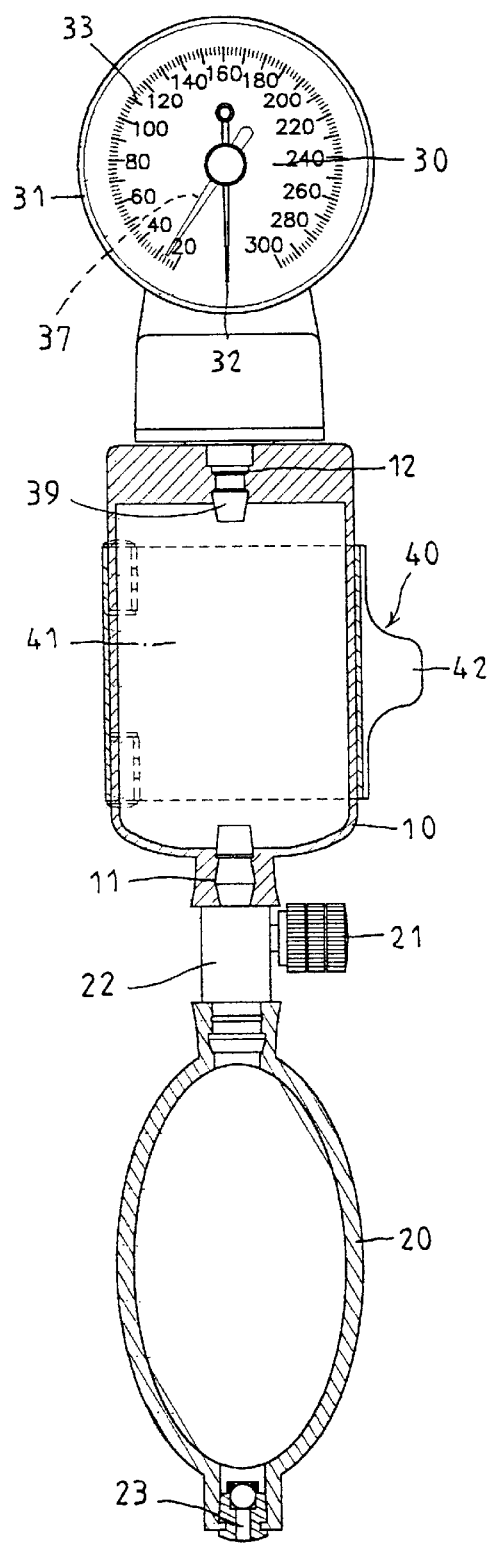
FIG. 5 is a partial cross sectional view taken along lines 5—5 of FIG. 1.

A pressure gauge 30 includes a coupler 39 engaged into the other port 12 of the bladder 10, for measuring or testing the pressure in the bladder 10 and the pumping device 20. A cover 31 may be attached to the front of the pressure gauge 30, such as rotatably received in a front and peripheral fence 34 of the pressure gauge 30, and may include a peripheral rib 35 engaged into a peripheral recess 36 of the fence 34 (FIGS. 3, 4).

The pressure gauge 30 includes a graduation 33 provided therein, and a pointer 37 rotatable relative to the graduation 33 to indicate the pressure value. Another pointer 32 is rotatably secured to the cover 31 with another knob 38 which may be used to rotate the pointer 32 relative to the graduation 33 to indicate the pressure value.

Figure 6:
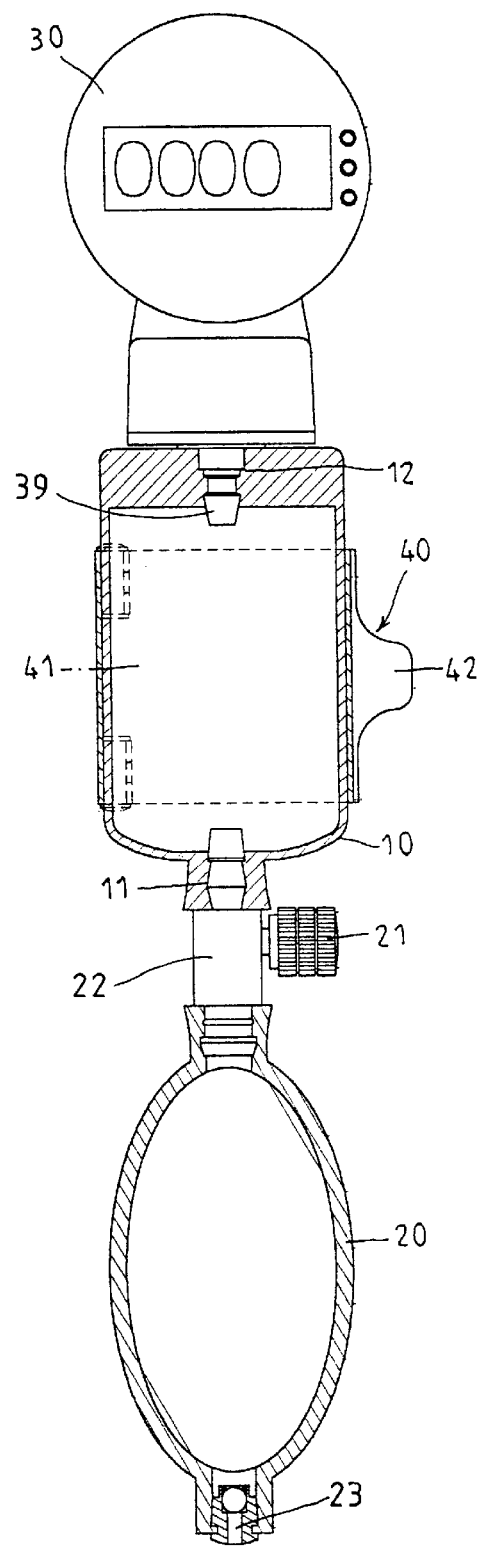
FIG. 6 is a partial cross sectional view similar to FIG. 5, illustrating another arrangement of the finger gripping force measuring or testing device.
Figure 7:
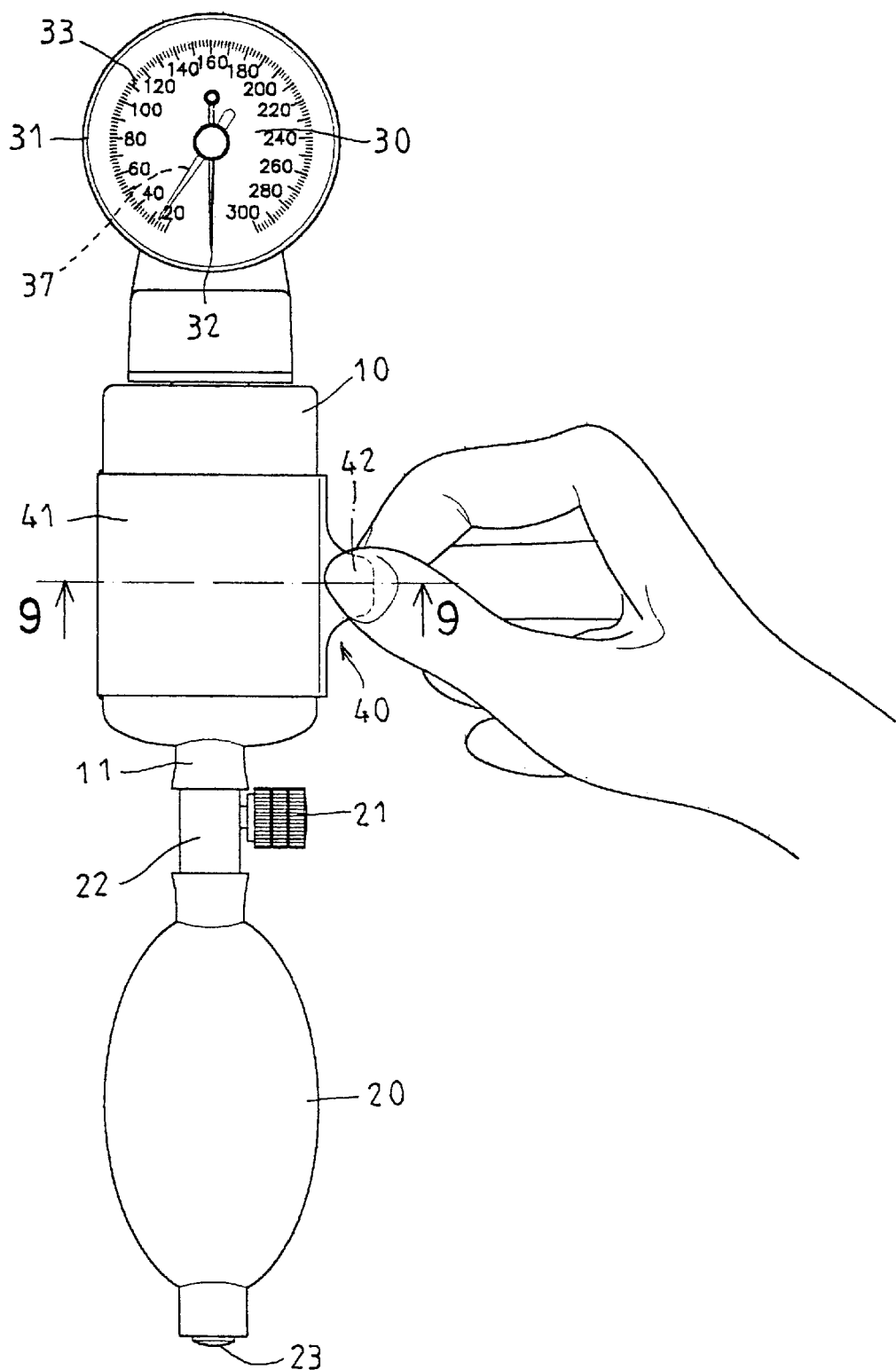
FIGS. 7 and 8 are plan schematic views illustrating the operation of the finger gripping force measuring or testing device.
Figure 8:
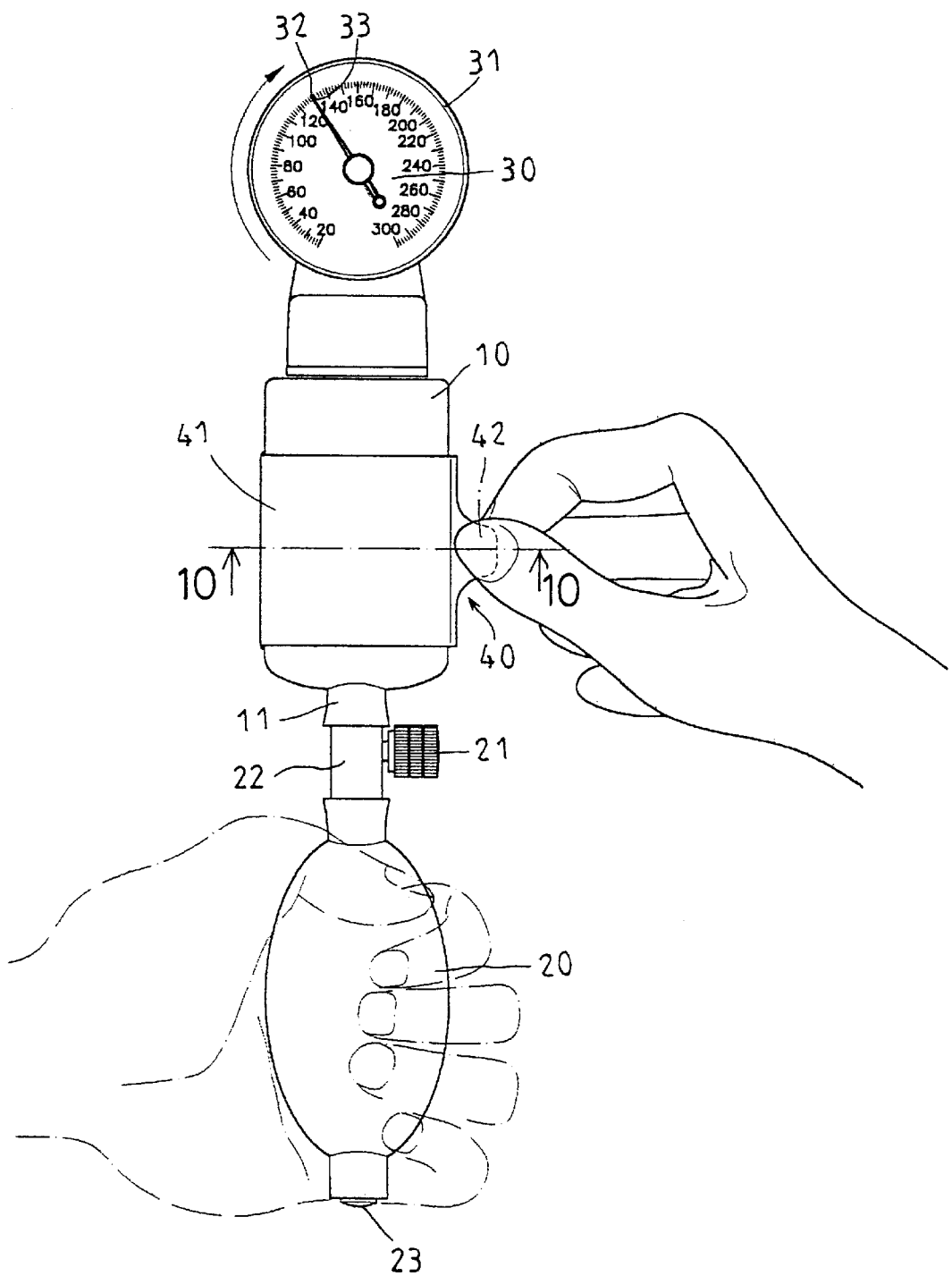
Figure 10:
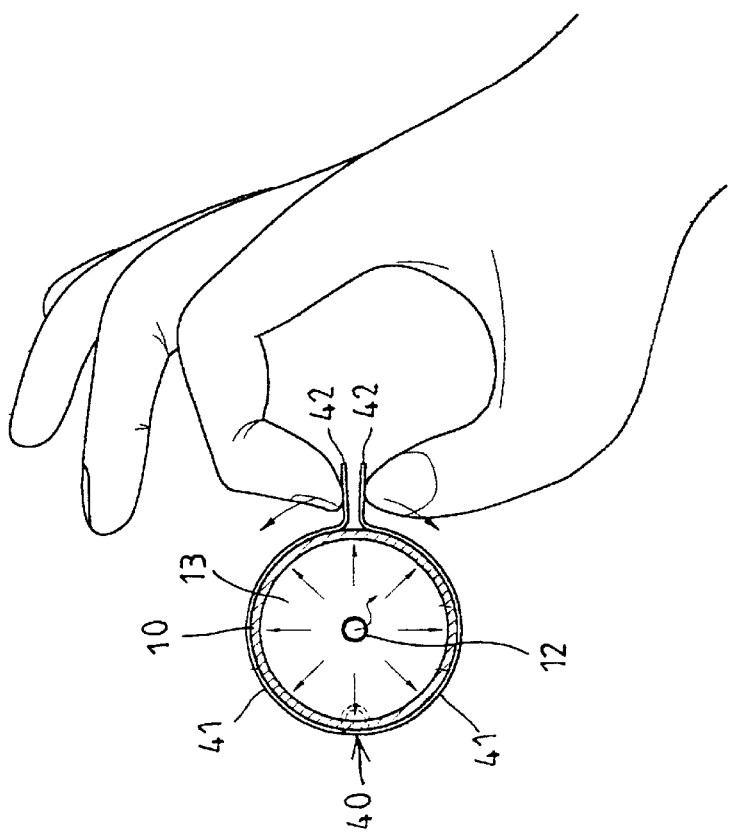
FIGS. 9, 10 are partial cross sectional views taken along lines 9—9, and 10—10 of FIGS. 7 and 8 respectively.
Figure 9:
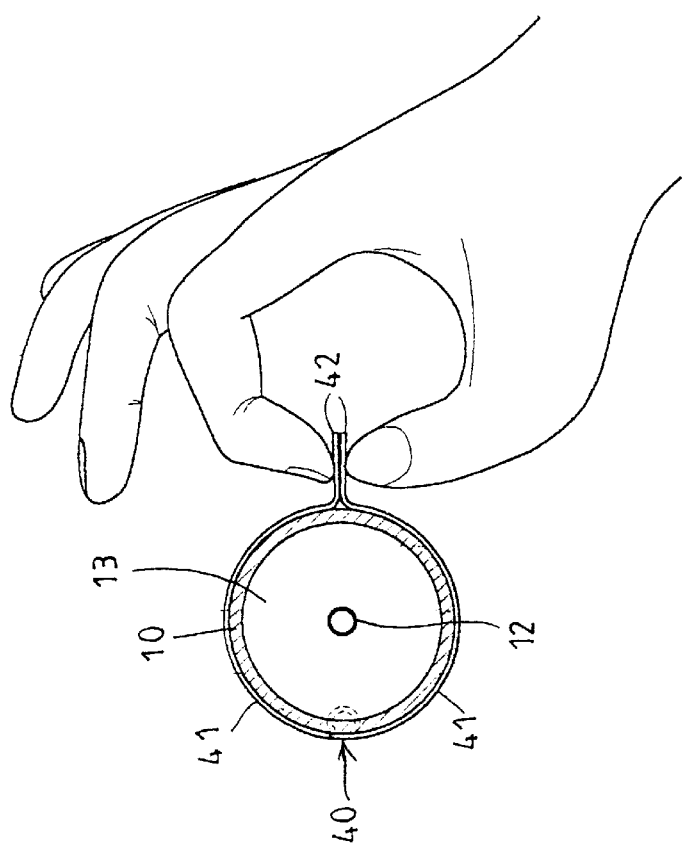
Figure 11:
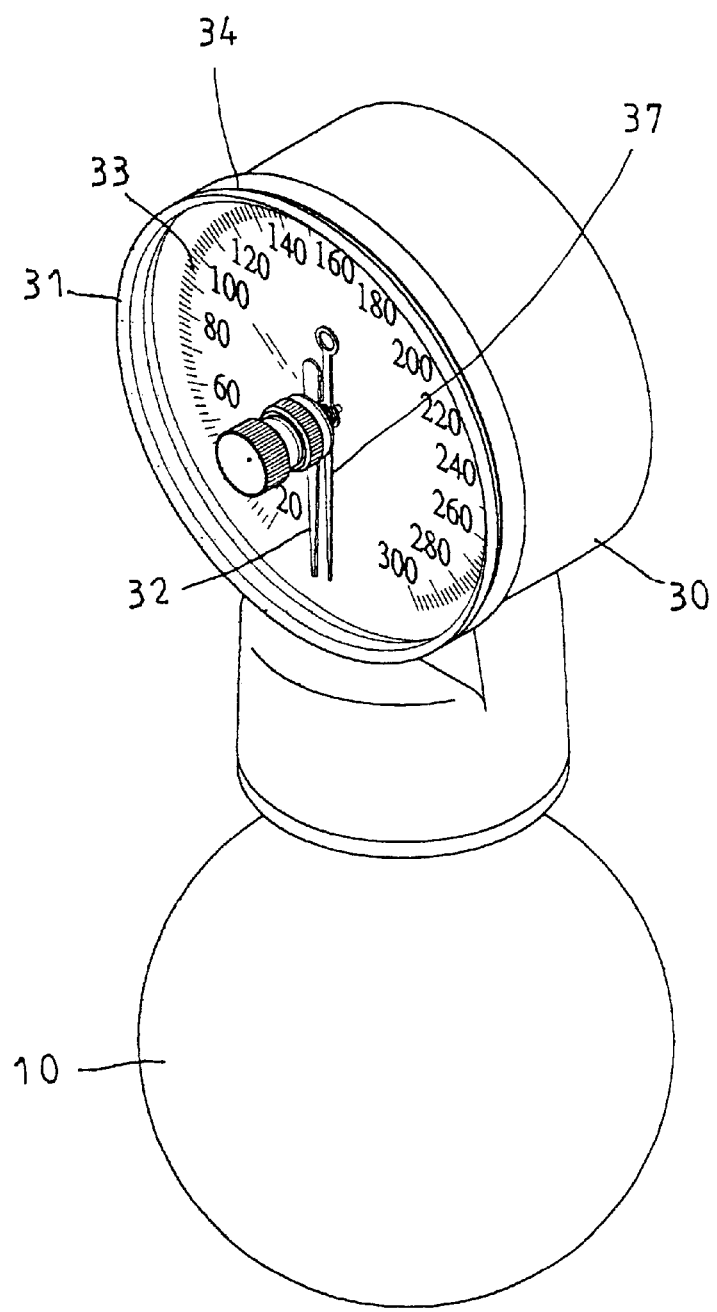
FIG. 11 is a perspective view illustrating another arrangement or embodiment of the finger gripping force measuring or testing device.
Figure 12:
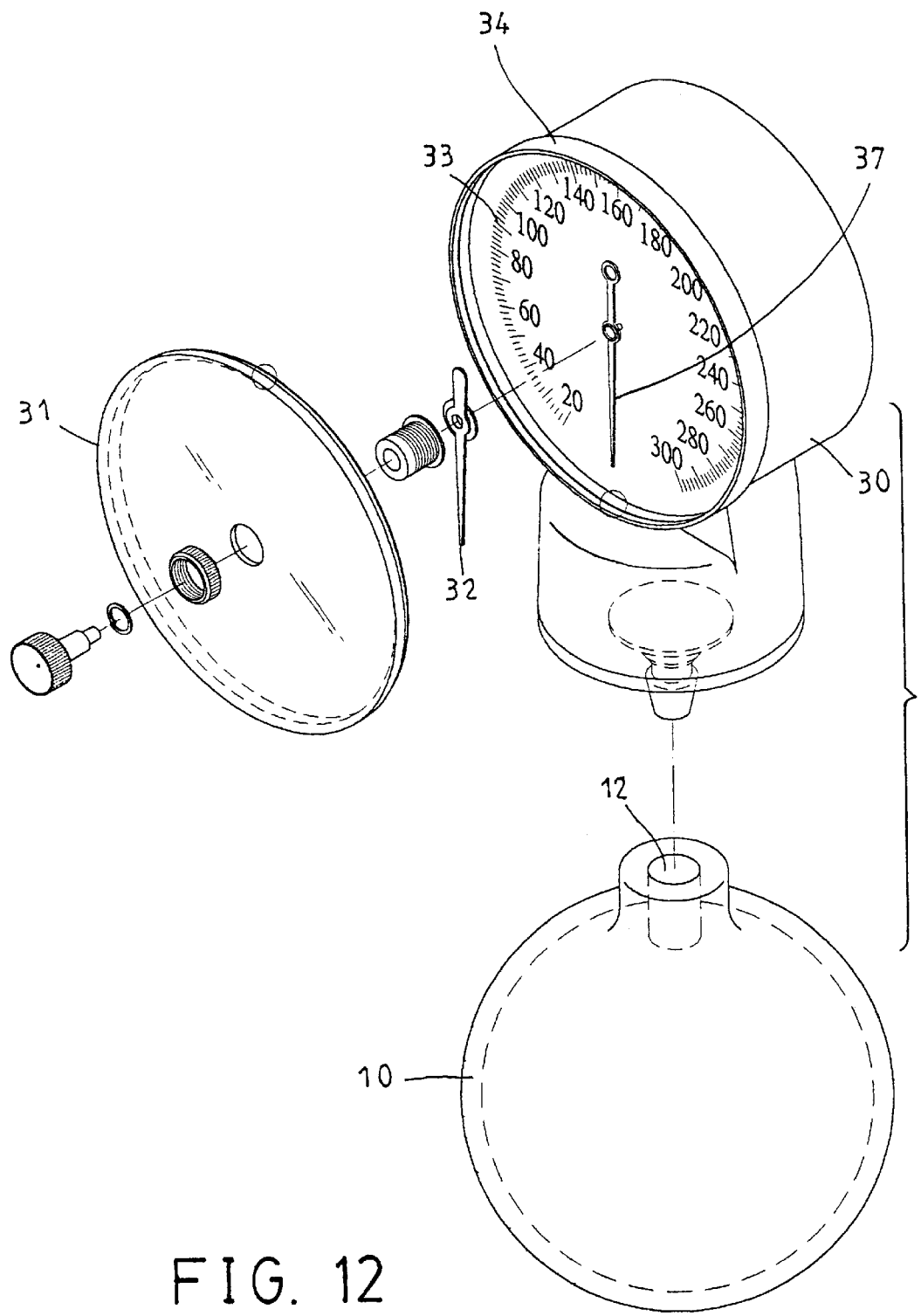
FIG. 12 is an exploded view of the finger gripping force measuring or testing device as shown in FIG. 11.
Figures 13, 14:
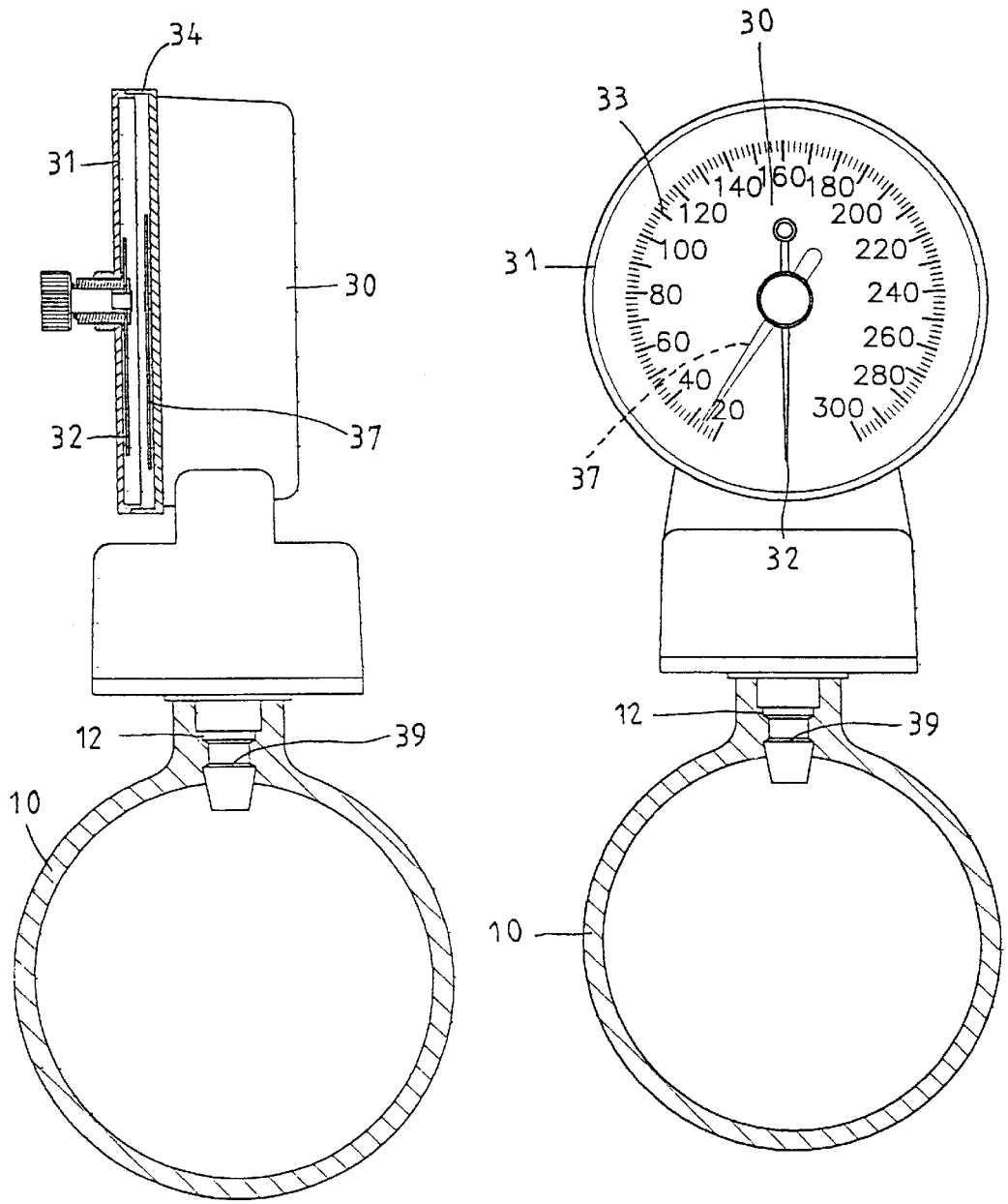
FIGS. 13, 14, 15, 16 are partial cross sectional views illustrating the operation of the finger gripping force measuring or testing device as shown in FIGS. 11 and 12.
Figure 17:
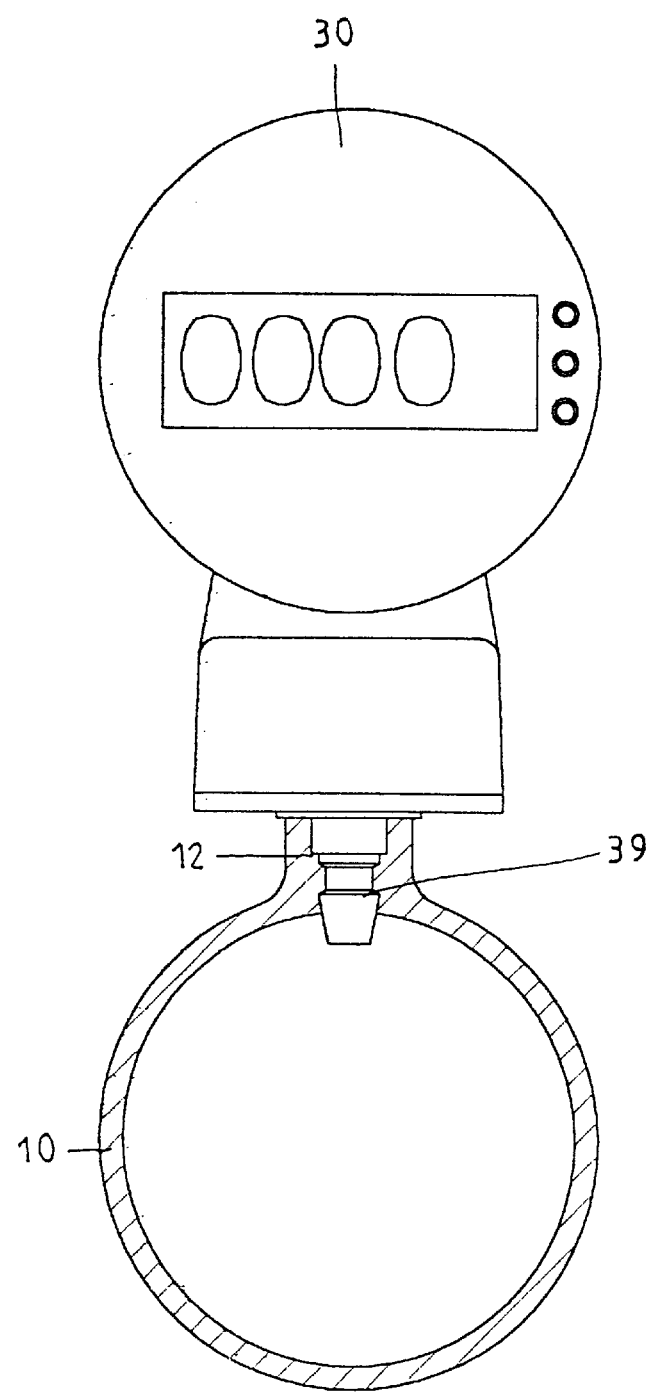
FIGS. 17, 18 are partial cross sectional views illustrating the other arrangement or embodiment of the finger gripping force measuring or testing device.
Figure 18:
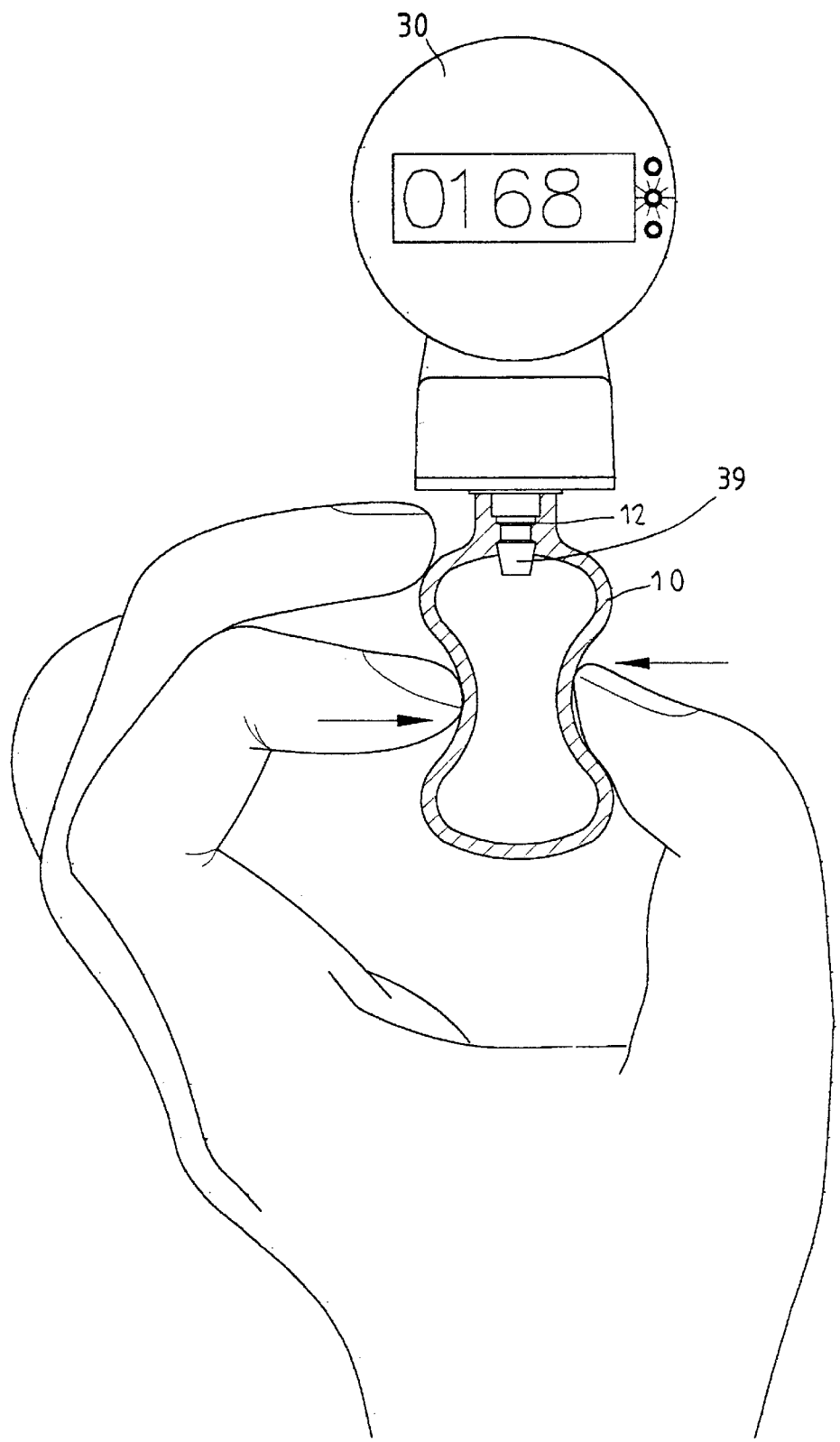
Figure 19:
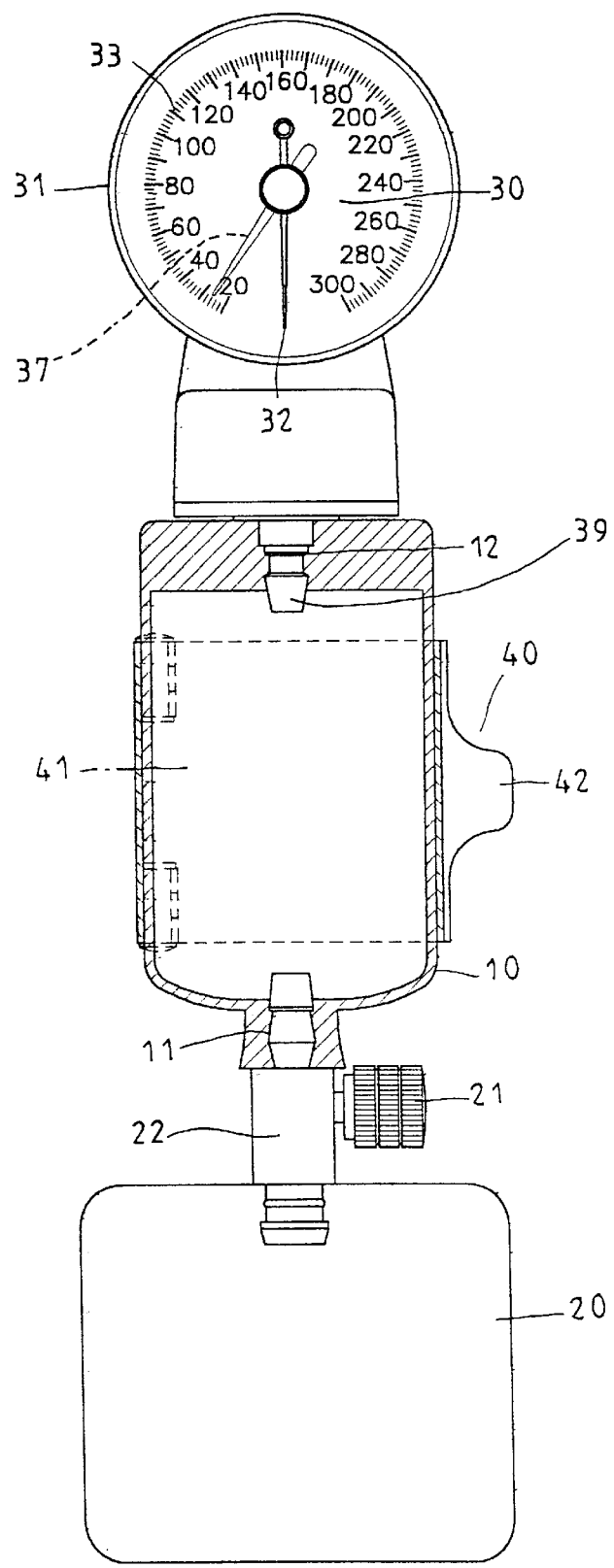
FIG. 19 is a further partial cross sectional view illustrating a still further arrangement or embodiment of the finger gripping force measuring or testing device.

Alternatively, the other types of pressure gauges 30 may also be provided and attached to the bladder 10, such as the digital or electrical type pressure gauges 30 as shown in FIGS. 6, 17, 18 may also be used to measure or test the pressure in the bladder 10 and the pumping device 20. Further alternatively, the other types of pumping devices 20, such as the mechanical pumping devices as shown in FIG. 19 may also be attached to the bladder 10, for pumping the bladder 10.

Alternatively, as shown in FIGS. 11–18, the bladder 10 may also be provided or formed with a predetermined pressure therein, and no pumping devices 20 are required to be attached or coupled to the bladder 10 to pump the bladder 10.

Figure 15:
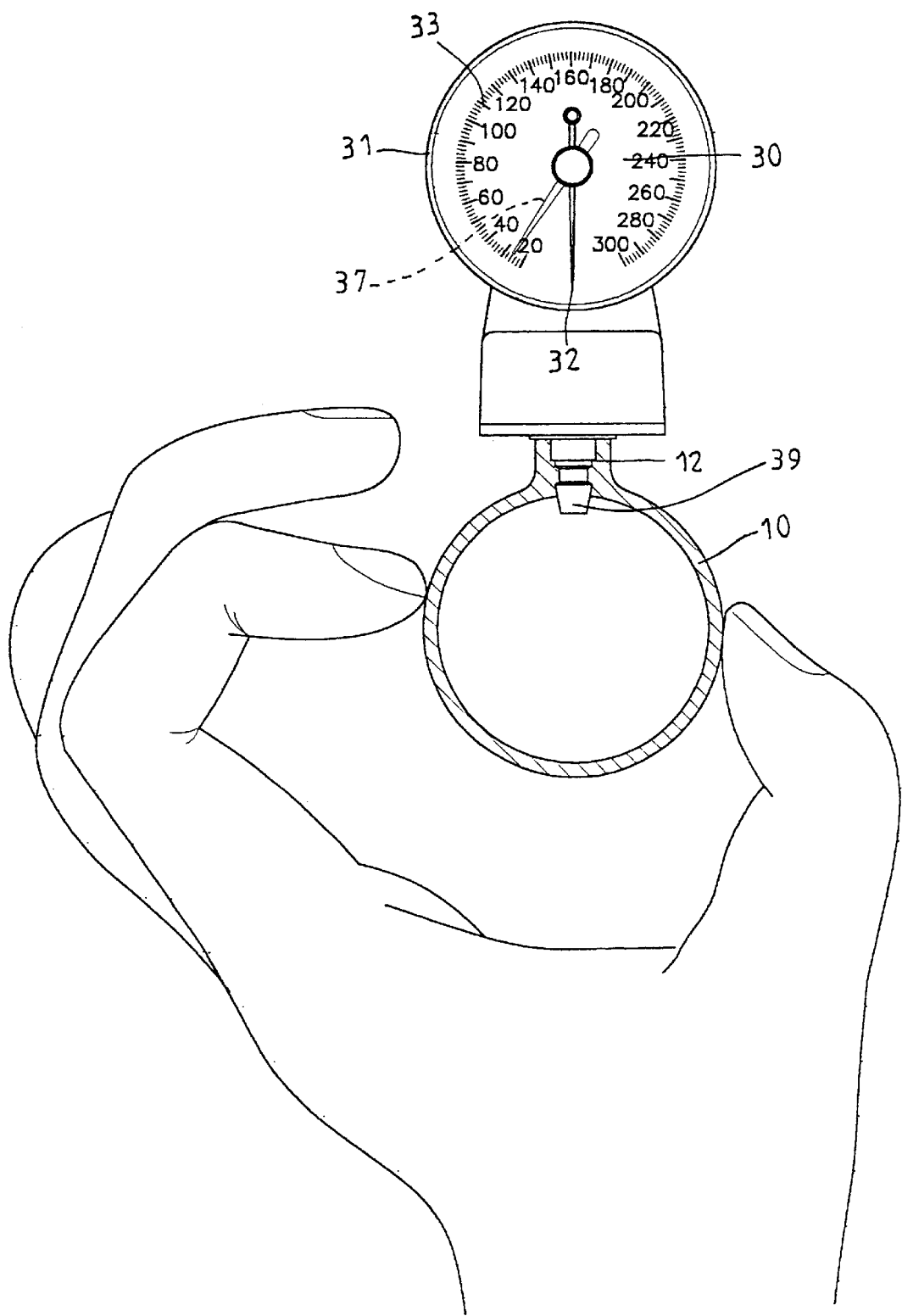
Figure 16:
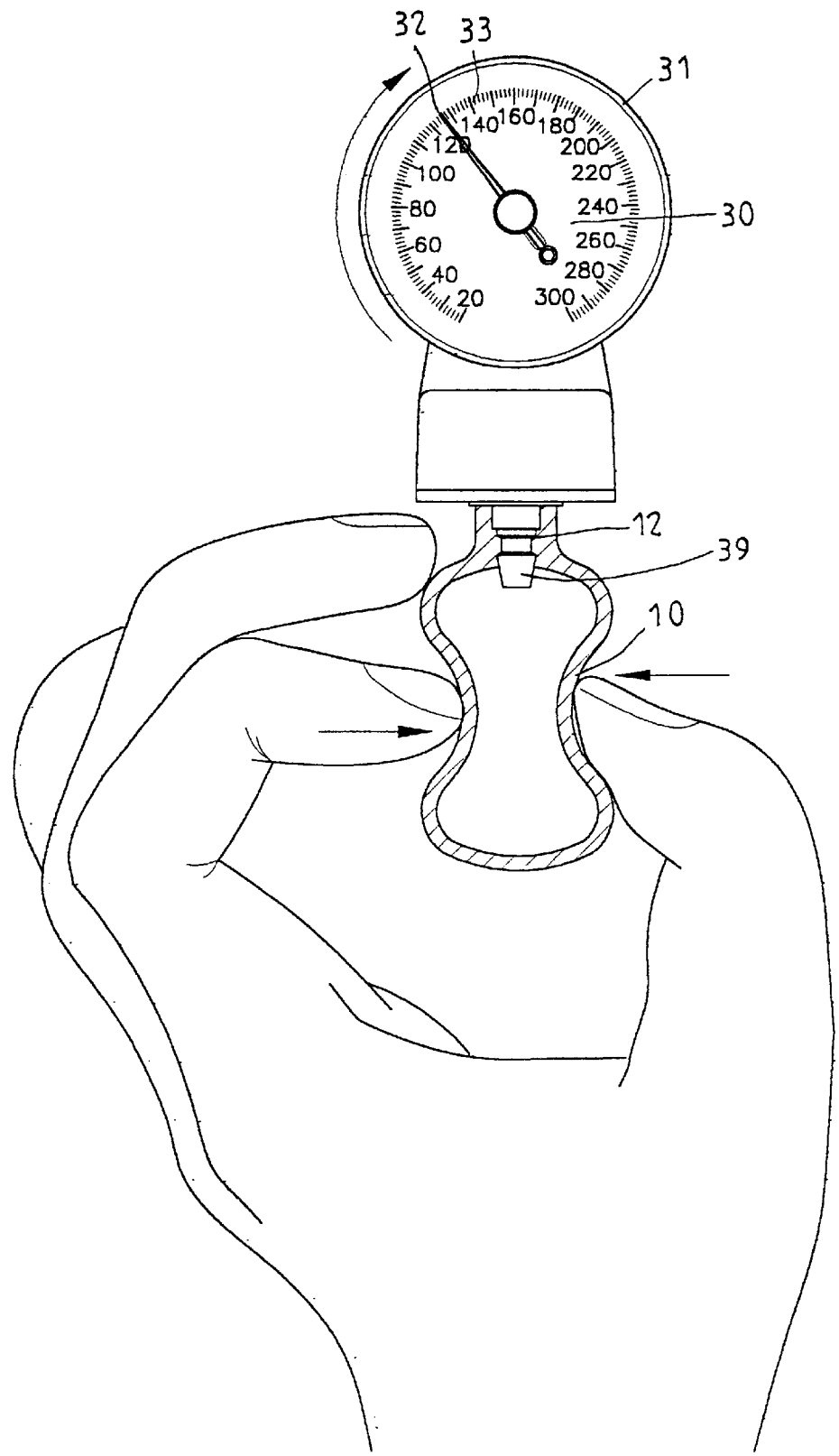

In operation, as shown in FIGS. 15, 16, 18, the users may compress or squeeze the bladder 10 with their fingers, in order to force air into the pressure gauge 30, which may thus be used to measure or to test the finger gripping force of the users. The provision or the attachment of the pumping devices 20 to the bladder 10 is to pump the bladder 10 to the required pressure therein, and for allowing the bladder 10 to be squeezed by the users.

Referring again to FIGS. 1, 2 and 5–10, the finger gripping force measuring or testing device further includes a pressing device 40 selectively or optionally attached onto the bladder 10 for compressing or squeezing or pressing the bladder 10.

For example, the pressing device 40 includes a pair of semi-cylindrical casings 41 having one side pivotally or rotatably secured together with one or more pivot joints 43 that form a pivot axle 43 for rotatably or pivotally securing the casings 41 together, and for allowing the casings 41 to be engaged onto the bladder 10.

The casings 41 each includes a flap 42 extended therefrom and preferably aligned with each other, and opposite to the joints or axle 43, for allowing the flaps 42 of the casings 41 to be compressed or forced toward each other against the resilience of the bladder 10 (FIGS. 7–10).

In operation, the pointer 37 of the pressure gauge 30 may be moved by squeezing the bladder 10 by one user. The pointer 32 of the cover 31 may then be rotated to indicate the pressure value obtained by the one user. The other user may then compress or squeeze the bladder 10 in order to force or to move or to rotate the pointer 32 to indicate another pressure value which may be compared with the previous pressure value indicated by the pointer 32, such that the gripping forces of the users may be compared with each other with the pointers 32, 37.

Accordingly, the finger gripping force measuring or testing device in accordance with the present invention may be used for measuring or testing the finger gripping forces of the users.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A testing device comprising:
   a pressure gauge,
   a bladder coupled to said pressure gauge, to force air to said pressure gauge, and
   a pressing device including a pair of casings engaged onto said bladder for pressing said bladder, and having a first side pivotally secured together, and having a second side,
   said bladder being provided to be squeezed by users with said pair of casings of said pressing device to measure gripping force of the users.

2. The testing device according to claim 1, wherein said bladder includes a port provided therein, said pressure gauge includes a coupler engaged into said port of said bladder.

3. The testing device according to claim 1 further comprising means for pumping said bladder.

4. The testing device according to claim 3, wherein said pumping means includes a pumping device coupled to said bladder to pump said bladder to required pressure.

5. The testing device according to claim 4, wherein said pumping means includes a valve coupled between said pumping device and said bladder.

6. The testing device according to claim 5, wherein said valve includes a knob attached thereto to control and to open and to close said valve.

7. The testing device according to claim 4, wherein said pumping device includes a check valve for allowing air to flow into said pumping device and for preventing air from flowing out of said pumping device.

8. The testing device according to claim 1, wherein said pressing device includes a flap extended from said second side of each of said casings, said flaps of said casings are arranged to be forced toward each other against said bladder.

9. The testing device according to claim 1, wherein said pressure gauge includes a front portion having a graduation provided thereon, and a pointer rotatably attached thereto to indicate said graduation.

10. The testing device according to claim 9, wherein said pressure gauge includes a cover attached to said front portion thereof, and a second pointer rotatably attached to said cover.

11. The testing device according to claim 10, wherein said cover includes a knob secured to said second pointer.

12. The testing device according to claim 10, wherein said pressure gauge includes a fence having a recess formed therein, said cover includes a rib rotatably received in said recess of said fence.

\* \* \* \* \*